(12) United States Patent
Bader

(10) Patent No.: US 6,908,767 B2
(45) Date of Patent: Jun. 21, 2005

(54) METHOD AND DEVICE FOR GROWING AND/OR TREATING CELLS

(76) Inventor: Augustinus Bader, Hinter den langen Hoefen 16, D-31275 Lehrte-Immensen (DE)

( * ) Notice: Subject to any disclaimer, the term of this patent is extended or adjusted under 35 U.S.C. 154(b) by 0 days.

(21) Appl. No.: 10/380,690

(22) PCT Filed: Aug. 8, 2001

(86) PCT No.: PCT/EP01/09159

§ 371 (c)(1),
(2), (4) Date: Apr. 22, 2003

(87) PCT Pub. No.: WO02/24861

PCT Pub. Date: Mar. 28, 2002

(65) Prior Publication Data

US 2003/0186217 A1 Oct. 2, 2003

(30) Foreign Application Priority Data

Sep. 19, 2000 (DE) .......................................... 100 46 175

(51) Int. Cl.⁷ ................................................ C12N 5/00
(52) U.S. Cl. ................. 435/395; 435/286.1; 435/297.5; 435/305.5
(58) Field of Search ............................. 435/395, 286.1, 435/297.5, 305.3

(56) References Cited

U.S. PATENT DOCUMENTS

| | | | |
|---|---|---|---|
| 5,462,874 A | 10/1995 | Wolf et al. | ............... 435/297.5 |
| 5,707,869 A | 1/1998 | Wolf et al. | .................. 435/401 |
| 6,093,551 A * | 7/2000 | Raithel et al. | .............. 435/7.21 |
| 6,277,642 B1 | 8/2001 | Mentzen et al. | ............... 436/54 |
| 6,468,792 B1 | 10/2002 | Bader | .......................... 435/325 |

FOREIGN PATENT DOCUMENTS

| | | | |
|---|---|---|---|
| DE | 295 19 602 U1 | 5/1996 | ............. B01L/7/00 |
| DE | 197 19 751 A1 | 11/1998 | ............. C12M/3/06 |
| DE | 199 35 643 A1 | 2/2001 | ............. C12M/3/00 |
| GB | 2 269 391 A | 2/1994 | ............. C12M/1/00 |
| WO | 97/33179 | 9/1997 | .......... G01N/35/00 |
| WO | 02/11880 A3 | 2/2002 | ............ B01J/19/00 |

* cited by examiner

*Primary Examiner*—James Ketter
(74) *Attorney, Agent, or Firm*—Davis & Bujold, P.L.L.C.

(57) ABSTRACT

The invention relates to a method for growing and treating cells in an automated manner, for diagnostic purposes. The inventive method involves a cell culture plate comprising a plurality of bore holes for receiving cells, the holes being open on the upper side of the cell culture plate and closed on the lower side of the same. Oxygen and nutrients are dynamically supplied to the bore holes used as cell culture chambers.

31 Claims, 4 Drawing Sheets

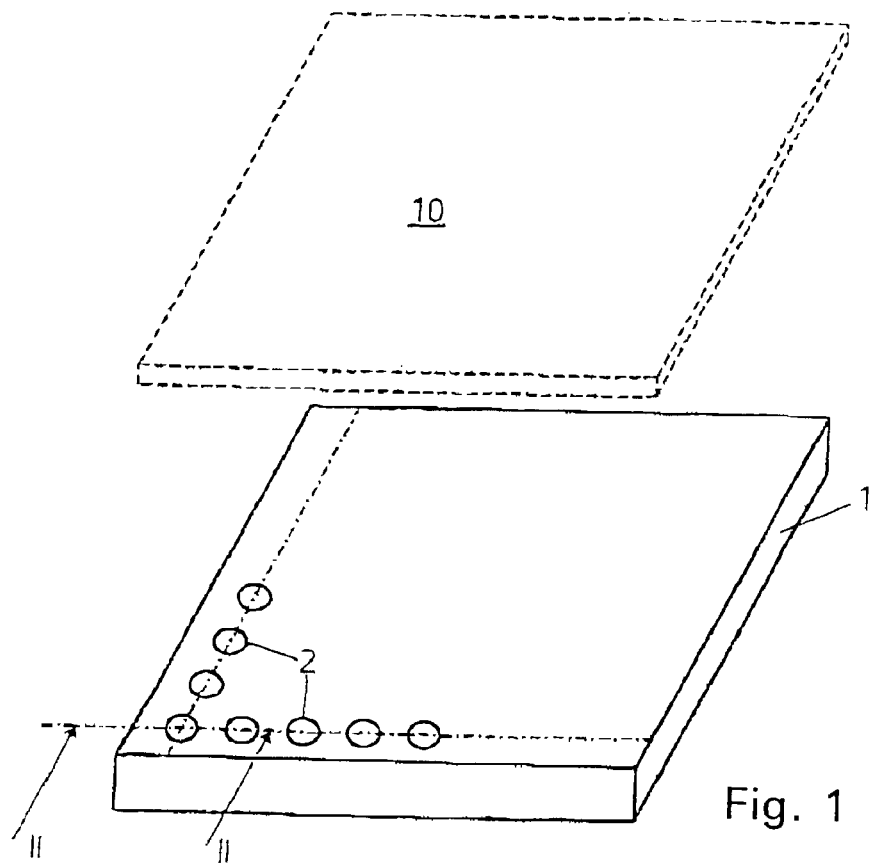
Fig. 1
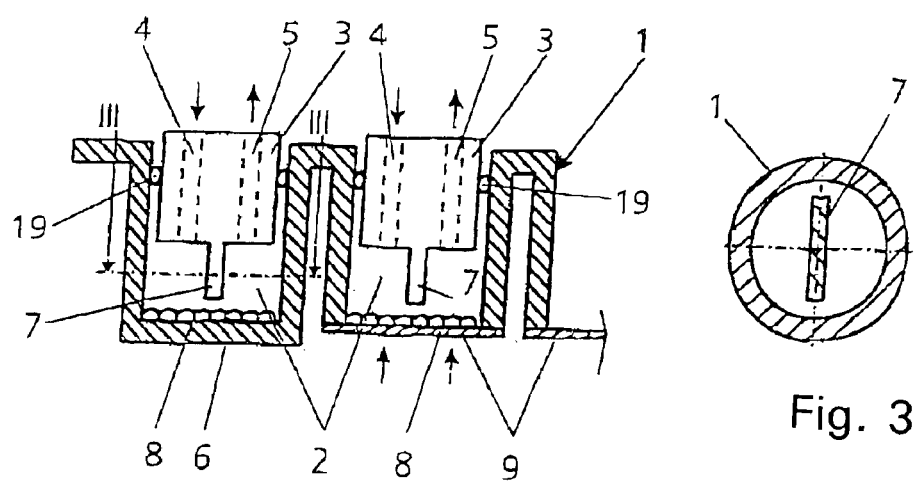
Fig. 2
Fig. 3

METHOD AND DEVICE FOR GROWING AND/OR TREATING CELLS

FIELD OF THE INVENTION

The invention relates to a method for growing and/or treating cells in an automated manner for diagnostic purposes. The invention furthermore also relates to a device for growing and/or treating cells and the use of a cell culture plate for this purpose.

BACKGROUND OF THE INVENTION

In the earlier DE 199 35 643.2 A1, a device for growing and/or treating cells is described, a moldable cell culture chamber being arranged on a carrier. The cell culture chamber is in this case formed by the carrier or a carrier film on one side and a cell culture film on the other side, which is elastic. Using a device of this type, it is possible to carry out a mass culture of cells with great variability and for many intended uses.

For further prior art, reference is made to DE 197 19 751 A1.

SUMMARY OF THE INVENTION

The present invention is based on the object of creating a method and a device for growing and/or treating cells in an automated manner, it being possible in a space which is as small as possible to grow and/or treat a high number of cells, which can also be of different type, for diagnostic purposes.

According to the invention, this object is achieved by the method mentioned in claim 1.

In claims 5 and 6, in each case a device for carrying out the method is described.

The use of a cell culture plate known per se to achieve the object set is shown in claim 13.

Cell culture plates of this type are known generally in medicine, in particular in pharmaceutical research, under the well plate or multiwell plate make. Here, cells for analytical tests are introduced into bores or hollows of the cell culture plate. The cells are then brought into contact with a very wide variety of substances by pipetting, and their actions on the cells are observed.

According to the invention, however, in complete modification of the previous use of a cell culture plate of this type, this is used for growing and/or treating cells in a dynamic method. This means, via the supply of oxygen and/or nutrients, which takes place continuously or alternatively batchwise, cells can now be grown and/or treated and observed over a longer period of time. The supply of nutrients and oxygen necessary for this can take place in a very varied way.

In a simple manner, nutrients and oxygen can here be led together through a continuous or alternatively batchwise perfusion of the hollows or bores now converted to cell culture chambers.

In a very advantageous embodiment of the invention, it is possible, however, to introduce a separate supply of oxygen into the cell culture chamber from the underside of the cell culture plate through a gas-permeable film or membrane. Normally, the cell culture plates are provided with stable, gas-impermeable bottoms. If these bottoms are now replaced by an appropriate gas-permeable film or membrane and an appropriate oxygen or air supply is provided to these areas, a simple and very intensive supply of oxygen is provided to the cells.

A further possibility for the supply of nutrients and/or oxygen can consist in that, in at least some of the bores or cell culture chambers of the cell culture plate, inserts can be employed which in each case are provided with supply bores and return flow bores.

BRIEF DESCRIPTION OF THE DRAWINGS

The invention will now be described, by way of example, with reference to the accompanying drawings in which:

FIG. 1 shows a cell culture plate (multiwell plate) in perspective view;

FIG. 2 shows a section according to the line II—II of FIG. 1 in magnified representation with the construction of the bores of the cell culture plate, in each case as a cell culture chamber;

FIG. 3 shows a section based on the line III—III of FIG. 2;

DETAILED DESCRIPTION OF THE INVENTION

Figure 4:
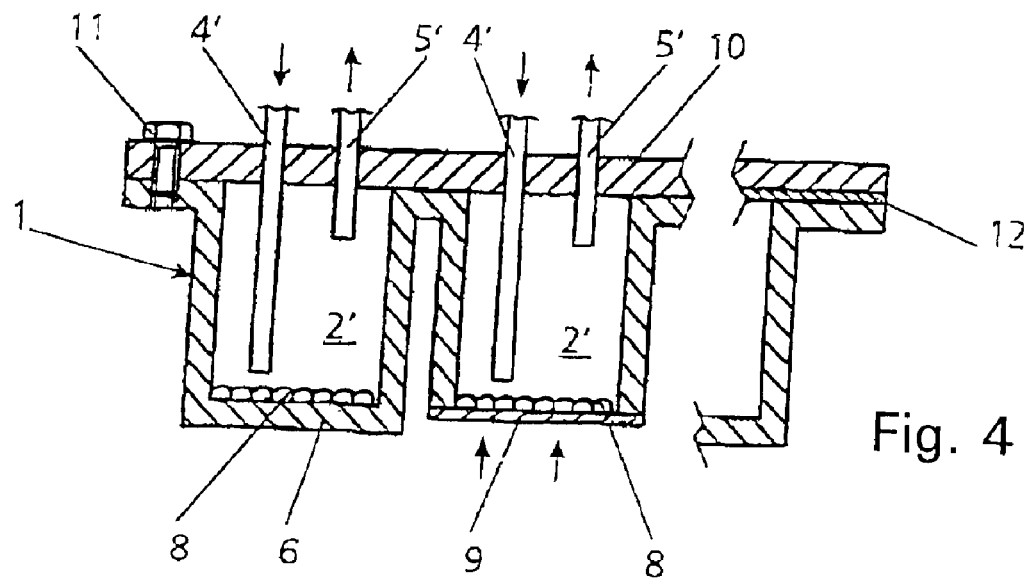
FIG. 4 shows an alternative embodiment of the construction of cell culture chambers in a section similar to that based on FIG. 2.

For growing and/or treating cells for diagnostic purposes, a cell culture plate 1 (multiwell plate) known per se is used, which in general has a high number of holes or bores 2 according to its size. The bores 2 have diameters of a few millimeters up to a number of millimeters, and their number can be up to several hundred units per cell culture plate 1.

From FIGS. 2 to 5, various embodiments of the bores 2 and their conversion to give cell culture chambers 2' are apparent. According to FIG. 2, in each bore 2 which is to serve as a cell culture chamber 2' an insert 3 is employed which is provided with a supply bore 4 and a return flow bore 5, which extend from the upper side of the cell culture plate 1 down to its underside, the undersides of the cell culture plate or the bores 2 being closed by bottoms 6. The inserts 3 are thus inserted from the upper side of the cell culture plate 1 into the open bores 2. For the sealing of the cell culture chambers 2', the inserts 3 are in each case provided on the peripheral side with a sealing ring 19.

From the side of an insert 3, in each case pointed to the bottom 6, a separating bridge 7 projects in the direction of the bottom 6. The separating bridge 7 lies between the supply bore 4 and the return flow bore 5 and extends, as is apparent from FIG. 3, straight across the bore 2. By means of the separating bridge 7, it is achieved that the nutrients introduced via the supply bore 4 cannot flow in a "short-circuit" directly to the return flow bore 3. By means of the separating bridge 7, they are forced, correspondingly, to flow through the entire cell culture chamber 2', and in the course of this to flow over the cells 8 applied to the bottom 6. At the same time, the separating bridge 7 can also serve for the centering or for the easier introduction of the insert 3 into the bore 2.

In the embodiment with the insert 3 shown in FIG. 2 on the left, the supply of oxygen to the cells 8 takes place together with the supply of nutrients via the supply bore 4. If the fixed bottom 6 is removed and this is replaced by a gas-permeable film or membrane 9 corresponding to the embodiment shown greatly enlarged in thickness on the right in the figure, a very intensive and direct supply of oxygen from the underside of the cell culture plate 1 through the gas-permeable film can take place (see arrows). The growth and the treatment of the cells 8 takes place on the gas-permeable film 9, which is shown significantly thicker in the figures for reasons of clarity.

FIG. 4 shows, instead of a large number of inserts 3 to be inserted into the bores 2, a cover plate 10, which is shown only very generally, marked with dashes, in FIG. 1. In the cover plate 10, supply connections 4' and return flow connections 5' are inserted into corresponding bores in the cover plate. As is apparent, the supply connections 4' project markedly deeper into the accompanying bores 2 or the cell culture chambers 2' in comparison with the return flow connections 5'. As is further apparent, by means of this measure it is likewise achieved that no short-circuit flow takes place directly from a supply to a return flow. The cells 8 are on the contrary flowed over by the nutrient medium. In FIG. 4, the two variants having a fixed bottom 6 and a gas-permeable film or membrane 9 are likewise shown next to one another.

On the left in FIG. 4, it is shown how the cover plate 10 is connected to the cell culture plate 1 by screws 11. On the right, it is shown that, instead of or additionally to a connection via screws 11, sealing by means of a sealing arrangement 12 between the cover plate 10 and the cell culture plate 1 can also be achieved.

Figure 5:
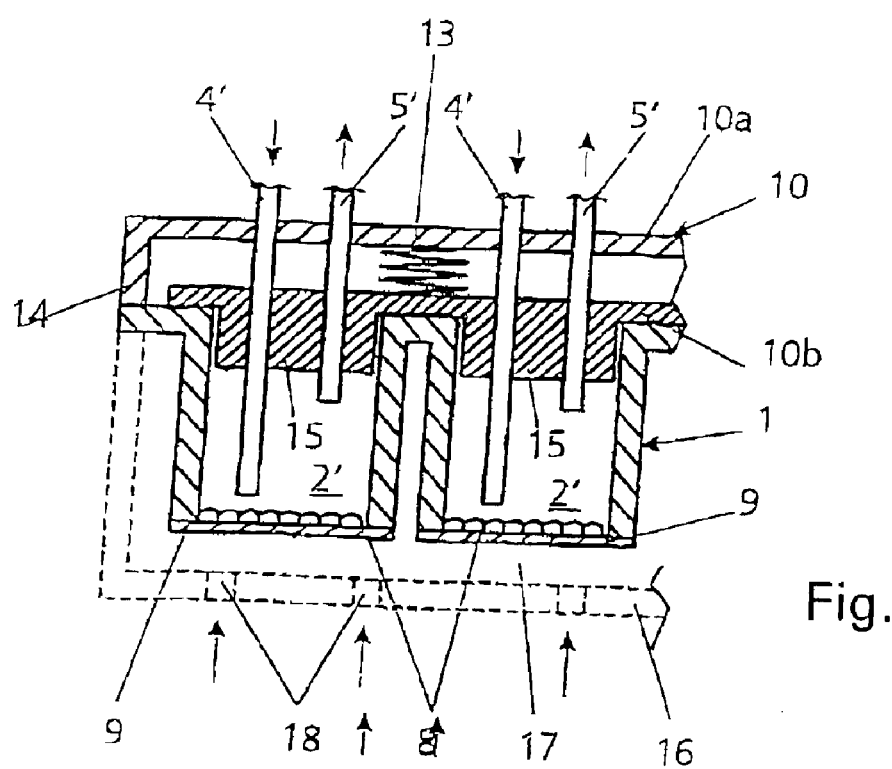
FIG. 5 shows a further embodiment for the formation of cell culture chambers, likewise in a section corresponding to that based on FIG. 2.

In FIG. 5, in principle, a two-part construction of the cover plate 10 with an upper cover 10a and a lower cover 10b is shown. As is apparent, the upper cover 10a and the lower cover 10b are connected to one another at an adjustable distance. By means of springs 13 placed between them, a pretension is achieved. The upper cover 10a is attached by means of bridges 14 to the edges of the cell culture plate 1 running round these. The lower cover 10b is provided with bores, through which supply connections 4' and return flow connections 5' are pushed, similarly to the embodiment according to FIG. 4. The supply connections 4' and return flow connections 5' are correspondingly also to be led out through the upper cover 10a either to its upper side or optionally also at the side on the edges. By means of the springs 13, a sealing of the cell culture chambers is achieved, because the lower cover 10b lies suitably tightly on the upper side of the cell culture plate 1. At the same time, extensions 15, which, on the underside of the lower cover 10b, project downward from this, are in this way also inserted into the bores 2 to form closed cell culture chambers 2'.

From FIG. 5, it is also apparent in the representation marked by dashes that the entire unit containing the cell culture plate 1 can be placed in a tank 16. The cell culture plate 1 is in this case attached running round tightly on the tank 16. Between the bottom formed in this case from a gas-permeable film or membrane 9 and the tank bottom is situated an interspace 17. If oxygen is introduced into the tank 16, e.g. via bores 18, a very intensive direct supply of oxygen for the cells 8 lying in the cell culture chambers 2' takes place through the film or membrane 9.

The bores 18 can preferably correspond to the size of the bores 2. The interspace 17 can optionally be inappropriate, in this case the cell culture plate 1 attaching directly to the bottom of the tank 16 and it being possible for an exchange of gas to take place via an opening, preferably corresponding to the diameter of the cell culture chambers 2', by means of a gas-permeable film 9 or membrane 9. The bores 18 in the tank 16 additionally make possible a visual improvement on microscopic observation of the cells. Preferably, for this the material of the cover plate 10 and also of the tank 16 is also produced from transparent material, such as, for example, polycarbonate or polystyrene.

Using the method and the device according to the invention, a type of bioreactor for growing and/or treating cells is [lacuna] from a cell culture plate 1 known per se. By means of the dynamic supply of nutrient medium and oxygen, a long-term culture is also possible here.

A further advantage of the invention is the possibility of automation of routinely proceeding processes, such as, for example, of any desired upwardly open culture vessels.

Cell culture plates of conventional construction known per se can also be modified for the method according to the invention in a simple manner. Thus it is possible, for example, to remove the fixed bottom 8 in a simple manner and to stretch a gas-permeable film 9 over the bores 2, which are now open on both sides, on the underside of the cell culture plate 1. By means of the gas-permeable film 9, the development of the cells 8 can also be observed if necessary, for which purpose the film 9 is to be designed to be suitably transparent.

In order that the cells 8 grow or are arranged in a very defined manner as a layer having a two-dimensional spread in the cell culture chambers 2', the entire cell culture plate 1 can, if necessary, also be frozen if it is wanted to transport or to store them intermediately until their use.

As a rule, all or a major part of the bores 2 of a cell culture plate will be converted to cell culture chambers 2' for the culture method. If necessary, it is, of course, also possible also to create only individual cell culture chambers 2' having correspondingly individual inserts 3, since the inserts 3 can also be employed on their own. The inserts 3 can also be flowed toward or emptied individually in separate culture units.

It is significant in each case that care is taken for an adequate supply of oxygen to the cells 8, in order also to be able to carry out a longer-lasting cell culture method, in particular for "demanding" cells. On the basis of the embodiment of the known cell culture plates 1, in particular of the bores 2, growth and/or treatment of cells in the form according to the invention was hitherto not possible.

Figure 6:
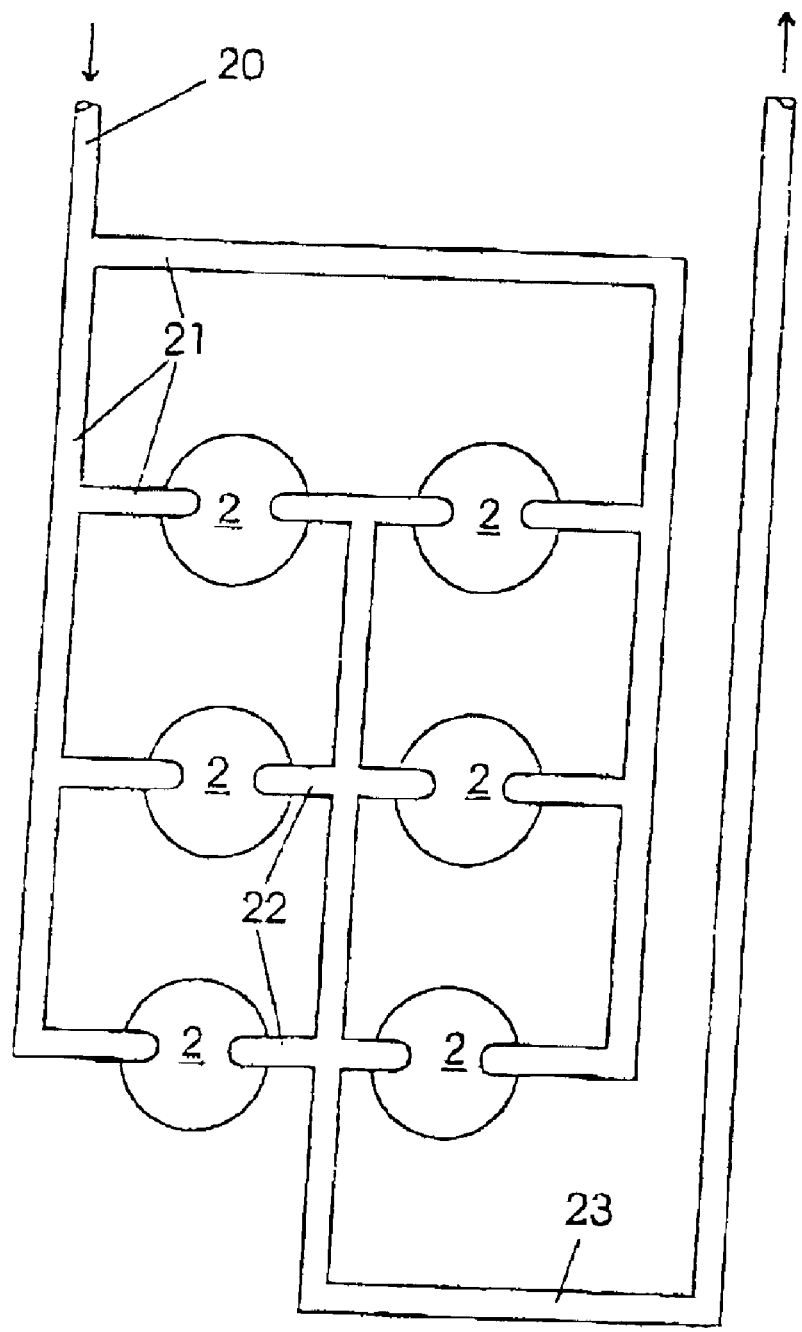
FIG. 6 in principle shows the supply to and removal of nutrients from the cell culture chambers in a plan view.

In FIG. 6, in principle the supply to and the removal of nutrients and optionally of oxygen from the cell culture chambers 2 is shown in a plan view. As is apparent, a common supply connection 20 is provided here, from which via a number of branch lines 21 the individual cell culture chambers 2 are supplied with nutrient medium and optionally also with oxygen. A joint removal via an outlet connection 23 then in turn follows via individual branch lines 22.

By means of the common supply connection 20 and the common outlet connection 23, the device can be used, for example, in the form of a "docking station", which is connected to a central station, possibly together with other devices. In this way, very large breeding stocks and/or growth devices can be created.

The joint supply and the joint removal using the branch lines 21 and 22 can take place, for example, through appropriate lines, openings or cannulas in the cover plate 10, from where the cell culture chambers 2 can in each case then be supplied separately via individual branch lines 21. In combination with the tank 16, in this way a type of cassette structure can be created. If necessary, a number of units can also be arranged one above the other. This is possible, for example, in that a number of cell culture plates 1 are arranged one above the other, it being possible to carry out the supply with nutrient medium and with oxygen through cover plates 10 lying in between, which are correspondingly provided, e.g. in each case on their upper side and on their underside, with common supply connections 20, branch lines 21 and 22 and common outlet connections 23.

Depending on the size of the cell culture chambers 2 and their number, it may optionally be necessary that a number of cover plates 10 with supply connections 20 arranged therein, branch lines 21 and 22 and outlet connections 23 are provided, which for reasons of space are provided with branch lines 21 and 22 arranged suitably displaced, in order that all cell culture chambers 2 can be supplied.

Additionally and alternatively, the cell culture plates 1 themselves can also be provided in each case with common supply connections 20, branch lines 21 and 22 and with common outlet connections 23, in order to be able to reach each cell culture chamber 2. For this, it is possible, for example, to divide a cell culture plate 1 in the middle and to introduce the flow channels in the area of the plane of separation. In each case, however, a channel guide should be created, by means of which a uniform supply of all cell culture chambers 2 is guaranteed.

The film or the membrane 9 can, if necessary, also be of microporous design, which has the advantage that nutrient medium can be brought into the cell culture chambers 2' not only from above, but additionally or alternatively also from below.

Figure 7:
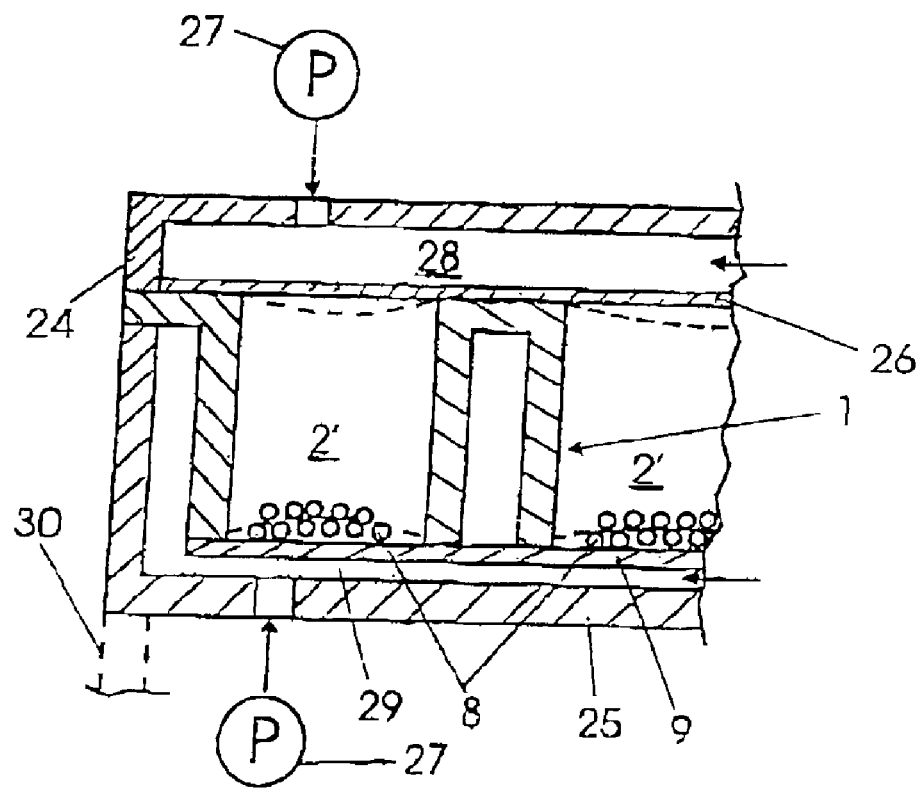
FIG. 7 shows, sector-wise, an embodiment where the cell culture chambers can be placed under pressure.

In FIG. 7, a very advantageous embodiment is shown, it being possible for the cell culture chambers 2' to be placed under pressure. For this, the cell culture plate 1 is closed off on the upper side by a pressure-tight dome 24 and on the underside by a pressure-tight container 25. The openings 2 on the upper side of the cell culture plate 1 are closed off using a flexible film 26, which if necessary can also be gas-permeable or microporous in order to achieve from this side a supply of the cells 8 situated in the cell culture chambers 2' with oxygen/air and/or nutrient medium. On the underside, the cell culture chambers 2' are likewise closed off by the membrane 9, which is of gas-permeable or microporous design.

By means of pressure connections 27 which are not shown in greater detail, a chamber 28 between the dome 24 and the film 26 and a chamber 29 between the membrane 9 and the bottom of the container 25 can be placed under elevated pressure or reduced pressure by means of appropriate pressure sources. The control of the pressure conditions is arbitrary here. This means pressure can be exerted alternately on the cell culture chambers 2' from above or from below or alternatively at the same time. For this, the film 26 and the membrane 9 are deformed correspondingly (see dashed representation). In this way, the cells 8 are accordingly moved mechanically, which has, for example, considerable advantages for the production of tissues, such as, for example, bone, cartilage, musculature and the like, since owing to extensions in the sense of conditionings or [lacuna], training can be simulated. Additionally, rhythmical or intermittent pressure loadings can be produced in the cell culture chambers 2'. By means of these measures, in vivo conditions can be simulated better.

By the use of the film 26, the cell culture chambers 2', if necessary, are also accessible to pipetting processes.

Instead of a simple film 26, the openings 2 can also be covered by a septum-like plastic membrane.

Instead of pressure loadings or alternatively additionally, electrical currents can be imposed on the cells 8. In this way, for example, extensions can also be induced by means of electromagnetic fields, which is advantageous, for example, for cardiac muscle cells, CNS cells (neuronal cells). In this way, for example, it is possible to test medicaments which accelerate or reduce the heart rate, for which purpose the electrical currents in practice electrically stimulate cardiac muscle cells. In this way, interactions occur between a technological and a biological system.

The cell culture systems described above can, if necessary, also be combined with one another in the form of a bioreactor or in a sandwich system. For this, it is only necessary to provide, instead of a tank 16 or the container 25, an appropriately shaped intermediate bottom, so that—as indicated marked by dashes in FIG. 7—a further unit 30 connects under the container 25 or under a corresponding intermediate bottom. At the same time, a number of units of this type can be arranged one above the other. The bioreactor resulting here can in this case be constructed in stage-like form or alternatively in mirror image form, a further unit connecting in mirror image form to the unit described in FIG. 7. In this case, the space 29 serves for the supply of air/oxygen and/or nutrient medium both for the cell culture plate 1 and for the cell culture plate (not shown) located in the unit 30. Of course, if necessary, however, separate supplies and outlets are also possible.

Instead of simple cells 8 in the cell culture chambers 2', multilayer cultures can, of course, also be grown.

One of the essential differences from the prior art to be retained is that the present cell culture system concerns dynamic processes which can proceed continuously or intermittently and not only static growing of cell culture systems, which after starting are no longer additionally treated.

Fundamentally, in the present system three methods with accompanying devices are present, namely:

1. In the simplest case closed bottoms are present and the supply of the cell culture chambers 2' takes place from above through the openings or bores 2 using corresponding supply bores 4 and return flow bores 5.

2. An embodiment of the cell culture plates 1 having a gas-permeable or microporous membrane 9 on the underside and closed-off bores 2 on the upper side, with or without supply bores 4 and return flow bores 5.

3. Elastic films both on the upper side and on the underside of the cell culture plate 1, which can be gas-permeable or microporous and which are loaded with appropriate pressures. The gas-permeable or microporous membranes 9 on the underside can be formed from a large number of individual membranes which in each case cover the cell culture chambers 2' on the underside. In general, however, a film is used which appropriately covers the entire underside of the cell culture plate 1, as is shown in FIG. 7.

According to the invention, complex cell culture systems, which place correspondingly higher demands on the microenvironment, can now be treated. At the same time, in the bores 2 of the cell culture plate 1, a 3-D structure having two-dimensional spread can also be defined, which corresponds in vivo to the separation of a capillary from the next capillary. This bioartificial tissue section serves for the production of organo-typical culture conditions in a very small space and thus makes possible even more complex coculture systems using various cell types and extracellular matrix to make high-throughput screening accessible.

Fundamentally, a thin-layer culture system is present in the method according to the invention, which is oxygenated from below in an advantageous way and which corresponds to the physiological cell density, namely in the distance of a blood capillary in the organism to the next blood capillary.

One of the main advantages of the present invention lies in the miniaturization with units which are as small as possible in a tight space. In this way, a small number of cells is also needed for a culture method, which can then be appropriately proliferated during the method.

One of the main areas of use of the method according to the invention and the device for this is therefore the investigation or the action of chemicals and pharmaceuticals on cells, in particular on human cells. In this way, animal experiments which are very complicated and expensive to carry out can be replaced at least partially.

What is claimed is:

1. A method for growing and/or treating cells for diagnostic purposes using a cell culture plate (1), which has a large number cell culture chambers (2'), open on an upper side of the cell culture plate (1) and closed on an underside thereof, in which cells are contained, having supply of oxygen and a flow of nutrients to cell culture chambers (2'), which are flowed through with at least the nutrients via supply bores (4) and return flow bores (5).

2. The method as claimed in claim 1, wherein the nutrients flow through the cell culture chambers (2') with or without oxygen.

3. The method according to claim 1, wherein the oxygen is introduced into the cell culture chambers (2') through a gas-permeable design of the bottom (6).

4. The method according to claim 1, wherein the bottoms (6) or a membrane (9) provided instead of the bottoms (6) are microporous.

5. The method according to claim 1, wherein the cell culture chambers (2') are pressurized with different pressures.

6. A device for
growing and/or treating cells for diagnostic purposes comprising a cell culture plate (1), which has a large number of cell culture chambers (2') open on an upper side of the cell culture plate (1) and closed on an underside thereof, in which cells are contained, having a supply of oxygen and a flow of nutrients to the cell culture chambers (2'), which are flowed through with at least the nutrients via supply bores (4) and return flow bores (5), and wherein at least some of the cell culture chambers (2) are closed on their undersides using gas-permeable or microporous films or membranes (9) as bottoms (6).

7. A device as claimed in claim 6, wherein
in at least some of the cell culture chambers (2') of the cell culture plate (1) inserts (3) can be employed, which are in each case provided with supply bores (4) and return flow bores (5).

8. The device as claimed in claim 7, wherein the inserts (3) are in each case provided on their sides pointing to the bottom (6) with a separating bridge (7) between the supply bores (4) and the return flow bores (5).

9. The device according to claim 8, wherein supply connections (4') and return flow connections (5') in each case extend from the supply bores (4) and return flow bores (5) toward the bottoms (6), the supply connections (4') and the return flow connections (5') in each case projecting into the cell culture chambers (2') to a different extent.

10. The device according to claim 7, wherein the inserts (3) are in each case provided with a sealing ring (19) on the peripheral side.

11. The device according to claim 6, wherein the cell culture plate (1) is covered with a cover plate (10).

12. The device according to claim 11, wherein the cover plate (10) is connected to the cell culture plate (1) by screws (11) and/or the cell culture plate (1) is sealed by a sealing arrangement (12).

13. The device according to claim 11, wherein the cover plate (10) is constructed in two parts, having an upper cover (10a) and a lower cover (10b), the two covers (10a, 10b) being connected to one another elastically or movably to one another.

14. The device according to claim 13, wherein the lower cover (10b) is provided with extensions (15) which project into at least some of the cell culture chambers (2'), and which are provided with supply connections (4') and return flow connections (5').

15. The device according to claim 10, wherein the cover plate (10) are provided with at least one supply connection (20), with branch channels (21, 22) and with at least one outlet connection (23) for the supply of the cell culture chambers (2) with nutrient medium and/or oxygen.

16. The device according to claim 15, wherein a number of cover plates (10) are provided for the supply of one or more cell culture plates (1).

17. The device according to claim 6, wherein the cell culture plate (1) is constructed in two parts, at least one supply connection (20), branch channels (21, 22) and at least one outlet connection (23) being provided in the separating plane.

18. The device according to claim 6, wherein the cell culture plate (1) is inserted into a tank (16).

19. The device according to claim 18, wherein the tank (16) is provided with oxygen supply lines and oxygen openings (18) in its wall.

20. The device according to claim 6, wherein the cell culture chambers (2') can be placed under variable pressure by means of pressure connections (27).

21. The device according to claim 20, wherein additionally to the elastic membrane (9), on the underside of the cell culture plate (1) the cell culture chambers (2') on the upper side of the cell culture plate (1) is covered with an elastic film (26), and in that interspaces (28, 29) above and below the cell culture plate (1) can be placed under pressure.

22. The device according to claim 6, wherein the cover plate (10) and/or the tank (26) or the container (25) are constructed as intermediate containers, and in that via the intermediate container one or more units (30) are connectable to common or to separate connections for the formation of a bioreactor.

23. The cell culture plate (1) according to claim 6, wherein the cell culture plate (1) is introduced into a tank (16) and is provided with a cover plate (10) and a tank bottom for automated perfusion.

24. A cell culture plate (1) for growing and/or treating cells for diagnostic purposes comprising a large number of cell culture chambers (2') open on an upper side of the cell culture plate (1), which are closed off on an underside thereof by bottoms (6), for growing and/or treating cells (8), which are introduced into the cell culture chambers (2'), in an automated manner for diagnostic purposes, wherein at least some of the bottoms (6) of the cell culture plate (1) are one of gas-permeable and microporous.

25. The method for growing and/or treating cells for diagnostic purposes according to claim 1, wherein the cell culture plate (1) is introduced into a tank (16) and is provided with a cover plate (10) and a tank bottom for automated perfusion.

26. The method for growing and/or treating cells for diagnostic purposes according to claim 1, wherein the cell culture plate (1) is frozen for purposes of transporting or storage prior to growing cells.

27. The method for growing and/or treating cells for diagnostic purposes according to claim 1, wherein the contained cells are moved mechanically within the bores by alternating pressure in the bores.

28. The method for growing and/or treating cells for diagnostic purposes according to claim 1, wherein the contained cells are moved by imposing electrical currents on the cells.

29. A method for growing and/or treating cells for diagnostic purposes using a cell culture plate (1), which has a large number of cell culture chambers (2') open on an upper side of the cell culture plate (1) and closed on an underside thereof, in which cells are contained, the method comprising the steps of supplying oxygen and a flow of nutrients to the cell culture chambers (2') and providing flow through of at least the nutrients via supply bores (4) and return flow bores (5), and introducing oxygen into the cell culture chambers (2') through gas-permeable bottoms (6) of the cell culture chambers (2').

30. A method for growing and/or treating cells for diagnostic purposes using a cell culture plate (1), which has a large number of cell culture chambers (2') open on an upper side of the cell culture plate (1) and closed on an underside thereof, in which cells are contained, the method comprising the steps of supplying oxygen and a flow of nutrients to the cell culture chambers (2') and providing flow through of at least the nutrients via supply bores (4) and return flow bores (5), and wherein the cell culture chambers (2') are pressurized with different pressures.

31. A method for growing and/or treating cells for diagnostic purposes using a cell culture plate (1), which has a large number of cell culture chambers (2') open on an upper side of the cell culture plate (1) and closed on an underside thereof, in which cells are contained, the method comprising the steps of supplying oxygen and a flow of nutrients to the cell culture chambers (2') and providing flow through of at least the nutrients via supply bores (4) and return flow bores (5), and wherein the cell culture plate (1) is introduced into a tank (16) and is provided with a cover plate (10) and a tank bottom for automated perfusion.

* * * * *